(12) United States Patent
Rößler et al.

(10) Patent No.: US 12,150,823 B2
(45) Date of Patent: Nov. 26, 2024

(54) METHOD TEMPOROMANDIBULAR JOINT RELATION AND TRANSFERRING IT INTO A VIRTUAL ARTICULATOR

(71) Applicant: DENTSPLY SIRONA inc., York, PA (US)

(72) Inventors: Friedemann Rößler, Bensheim (DE); Johannes Rücker, Zwingenberg (DE)

(73) Assignee: DENTSPLY SIRONA INC., York, PA (US)

( * ) Notice: Subject to any disclaimer, the term of this patent is extended or adjusted under 35 U.S.C. 154(b) by 507 days.

(21) Appl. No.: 17/430,886

(22) PCT Filed: Feb. 18, 2020

(86) PCT No.: PCT/EP2020/054224
§ 371 (c)(1),
(2) Date: Aug. 13, 2021

(87) PCT Pub. No.: WO2020/169596
PCT Pub. Date: Aug. 27, 2020

(65) Prior Publication Data
US 2022/0079722 A1 Mar. 17, 2022

(30) Foreign Application Priority Data
Feb. 19, 2019 (EP) .................................... 19020077

(51) Int. Cl.
*A61C 13/00* (2006.01)
*A61B 5/00* (2006.01)
(Continued)

(52) U.S. Cl.
CPC ........ *A61C 13/0004* (2013.01); *A61B 5/0088* (2013.01); *A61C 7/002* (2013.01);
(Continued)

(58) Field of Classification Search
CPC ... A61C 13/0004; A61C 7/002; A61C 9/0006; A61C 9/0046; A61C 11/00;
(Continued)

(56) References Cited

U.S. PATENT DOCUMENTS

9,380,986 B2 * 7/2016 Lähelmä ................ A61B 6/145
10,492,895 B1 * 12/2019 Alzain ................ A61C 19/045
(Continued)

*Primary Examiner* — Thomas C Lee
*Assistant Examiner* — Tyler Dean Hedrick
(74) *Attorney, Agent, or Firm* — DENTSPLY SIRONA INC.

(57) ABSTRACT

The present invention relates to method of measuring patient-specific temporomandibular joint relation and transferring it into a virtual articulator by using a device comprising: a transfer linkage which can be attached from its upper end to a face bow; an impression means for holding impression material and for taking the impression of the upper jaw and/or the lower jaw of the patient through said impression material; at least a first form-fitting component fixed at the lower end of the transfer linkage, for leaving an impression on the impression material to be placed on the grip of the impressions means projecting out of the mouth of the patient.

19 Claims, 8 Drawing Sheets

(51) Int. Cl.
*A61C 7/00* (2006.01)
*A61C 9/00* (2006.01)
*A61C 11/00* (2006.01)
*A61C 19/045* (2006.01)
*G16H 20/40* (2018.01)
*A61B 18/20* (2006.01)

(52) U.S. Cl.
CPC .......... *A61C 9/0006* (2013.01); *A61C 9/0046* (2013.01); *A61C 11/00* (2013.01); *A61C 19/045* (2013.01); *G16H 20/40* (2018.01); *A61B 2018/20353* (2017.05)

(58) Field of Classification Search
CPC ..... A61C 19/045; A61C 19/04; A61B 5/0088; A61B 2018/20353; G16H 20/40; G16H 30/00; G16H 50/50; G06T 1/0007; G06T 17/00; G06T 2207/30036
See application file for complete search history.

(56) References Cited

U.S. PATENT DOCUMENTS

| | | | | |
|---|---|---|---|---|
| 2016/0291485 | A1* | 10/2016 | Funayoshi | G03F 7/0002 |
| 2019/0290408 | A1* | 9/2019 | Fisker | A61C 11/00 |
| 2023/0320823 | A1* | 10/2023 | Marshall | A61C 19/045 |
| | | | | 433/69 |

* cited by examiner

METHOD TEMPOROMANDIBULAR JOINT RELATION AND TRANSFERRING IT INTO A VIRTUAL ARTICULATOR

CROSS-REFERENCE TO RELATED APPLICATIONS

This patent application is a National Phase application of International Application No. PCT/EP2020/054224 filed Feb. 18, 2020, which claims the benefit of and priority European Patent Application Number 19020077.4 filed on Feb. 19, 2019, which is herein incorporated by reference for all purposes.

TECHNICAL FIELD OF THE INVENTION

The present invention relates to virtual and physical articulators for simulating chewing motion of dental prostheses, particularly digitally constructed dental prostheses, based on temporomandibular joint relationship. The present invention more particularly relates to a method and device for measuring patient-specific temporomandibular joint relation and transferring it into a virtual or physical articulator.

BACKGROUND OF THE INVENTION

To measure the temporomandibular joint (TMJ) relation, articulators are used in dental technology. These reflect the static and dynamic relation of the patient's jaw to the TMJ and simulate chewing movements. The chewing movements are used to make all dental prostheses as optimal as possible so that the patient is not bothered when biting with the dental prosthesis and a correct bite is guaranteed. To use the physical articulator, the plaster models of the upper and lower jaw must be mounted in the final bite position (occlusion) in the physical articulator. The position in the physical articulator is ideally determined by measuring the patient-specific temporomandibular joint relation. If no measurement data is available, the position of the jaw in the articulator is estimated according to a standard procedure and the settings of the articulator are selected according to an average dentition (the so-called medial articulation).

Figure 1:
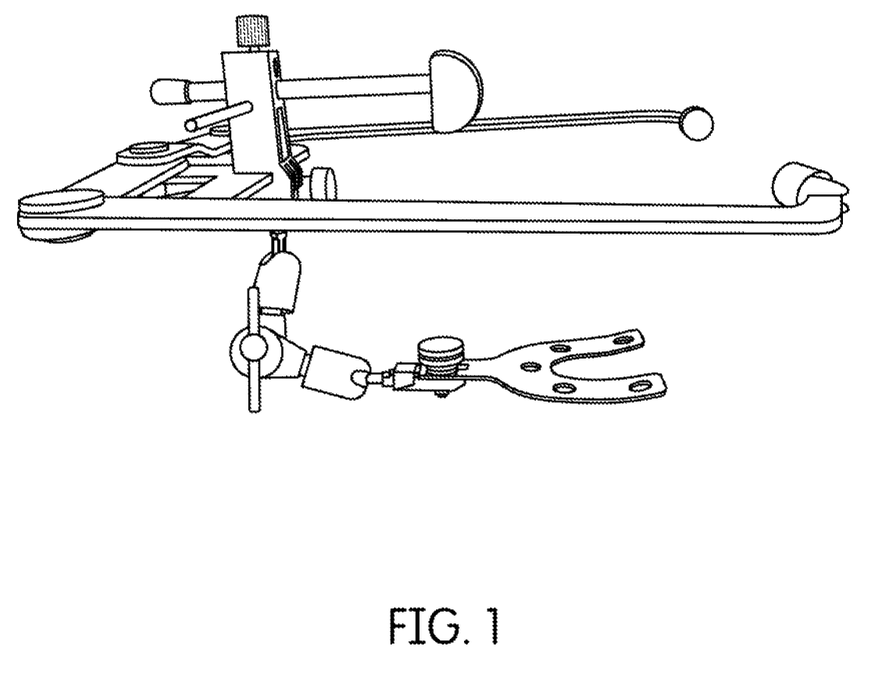
Figure 2:
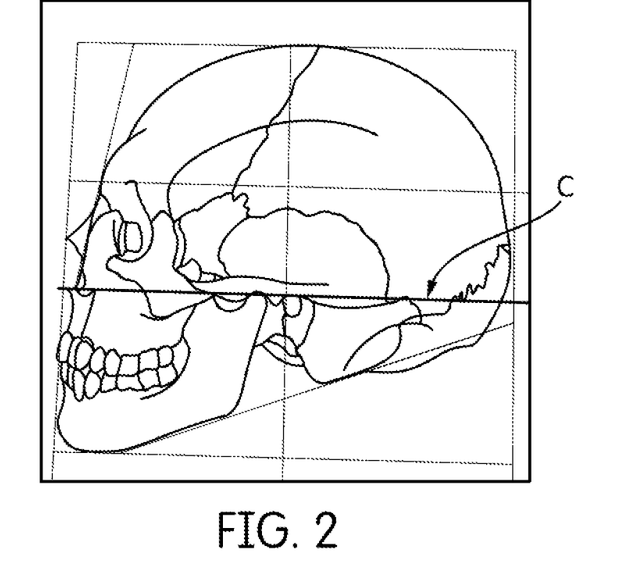
FIG. 2—is a schematic view of the Camper's plane as cranial reference plane for the orientation of the upper jaw.
Figure 3:
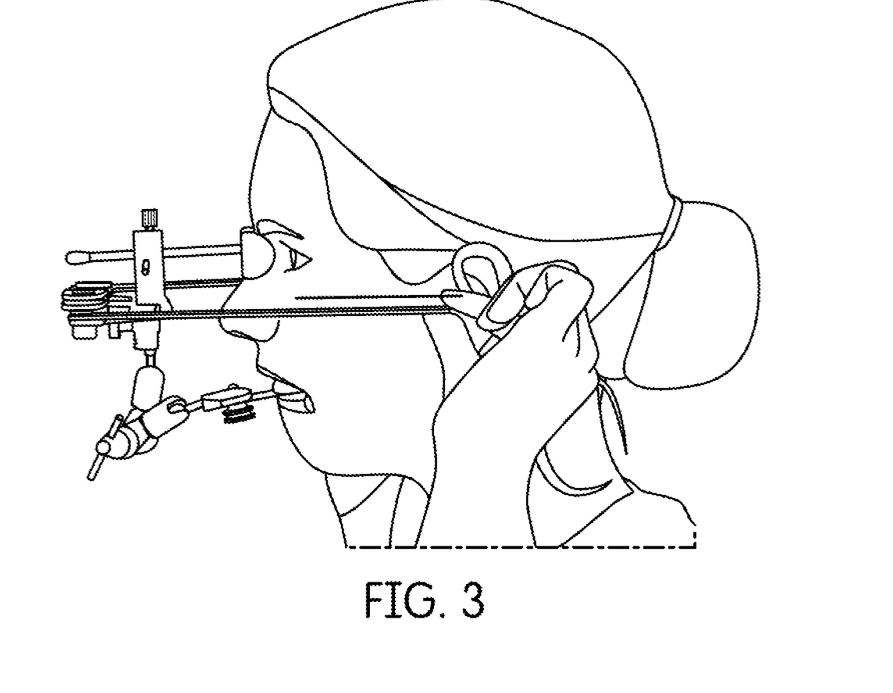
FIG. 3—is a schematic view of the face bow, the transfer linkage and the bite fork of FIG. 1 according to the prior art as attached to a patient's head.
Figure 4:
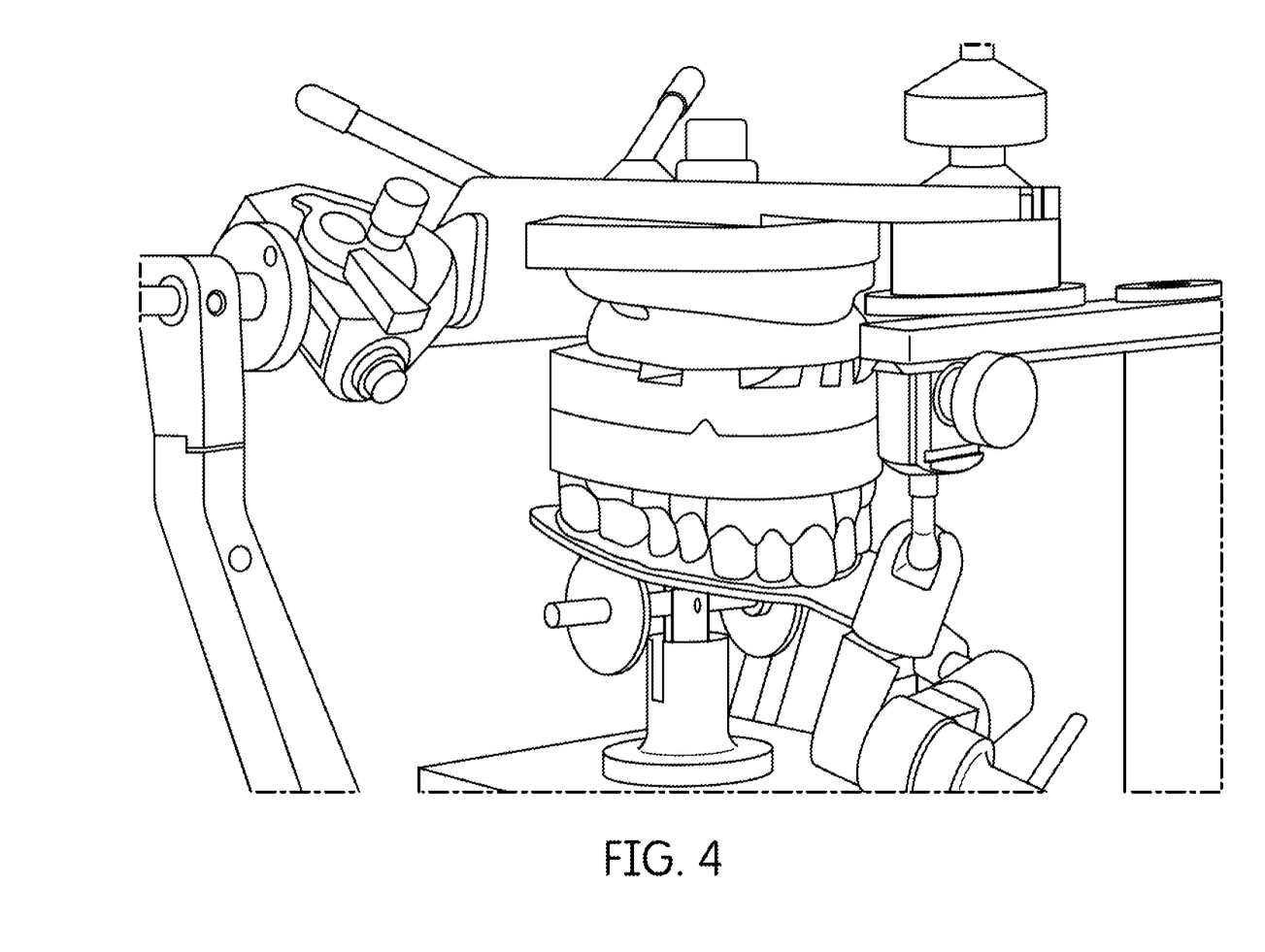
FIG. 4—is a schematic view of the transfer linkage and the bite fork attached into a physical articulator, wherein the upper and lower jaw models are plastered in their correct positions according to the prior art.

For optimal dental prostheses, it is advantageous to determine the patient-specific parameters and transfer them to the articulator. Of importance is the relation of the upper jaw which is firmly connected to the cranial bone, to the temporomandibular joints. To determine this relation a so-called face bow is used (FIG. 1). This face bow is attached to the patient's head so that it lies in a given cranial reference plane, e.g. the Camper's plane (FIG. 2) or the Frankfort Plane. For this purpose, the face bow is usually aligned to the eyes, bridge of the nose and outer ear canal, which are approximately at the level of the temporomandibular joints and fixed (FIG. 3). Then the relation to the upper jaw is determined with the help of an impression means such as the bite fork. This is attached by means of impression material on the upper jaw. The bite fork is connected via a movable linkage with the face bow. As soon as the position of the bite fork and face bow is correctly set, the movable linkage is fixed so that both units are connected in a fixed relation. Then the linkage and the bite fork are sent to the laboratory. In the laboratory, the bite fork-linkage assembly can now be attached to a suitable physical articulator using a special transfer device, and the plaster model of the upper jaw can be transferred (plastered in) to the physical articulator at the correct position known via the bite fork (FIG. 4).

Figure 5:
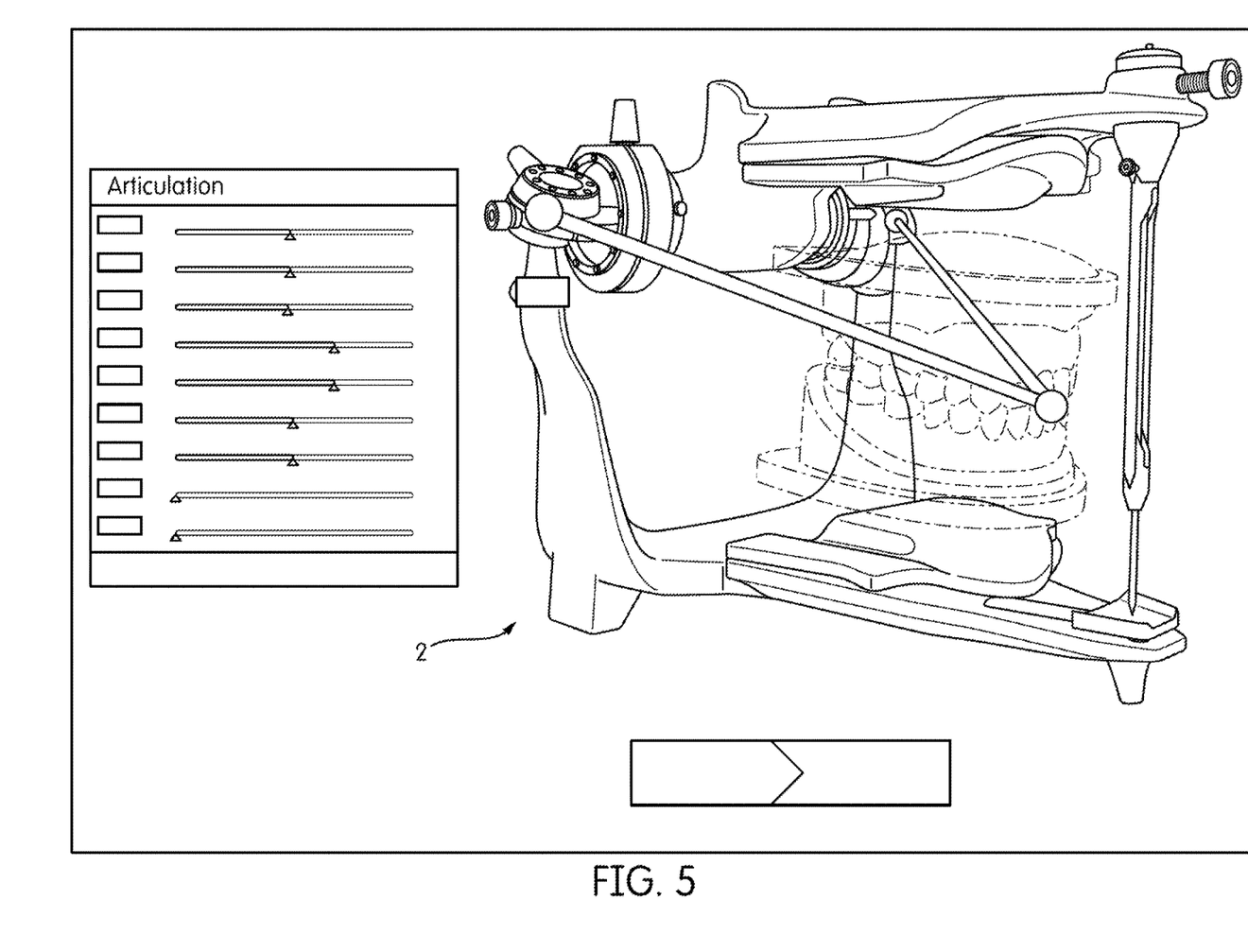
FIG. 5—is a schematic view of a virtual articulator from the inLab software.

The CAD/CAM technology also uses virtual articulators (FIG. 5) which like their physical counterparts can be used to simulate the chewing motion of the digitally constructed dental prostheses. As for the physical articulators, it is also advantageous for the virtual articulators to set them up as patient-specific as possible. Here, too, the correct setting of the respective cranial reference plane and the relation of the upper jaw model to the temporomandibular joints is of importance.

When using the inLab and CEREC software by Dentsply Sirona, the parameters of the virtual articulator have hitherto been determined manually and set via sliders on the user interface. The orientation of the occlusal plane and the determination of the incisal point is performed manually in the model axis step. This orientation can only be made based on the recorded jaw models. A reference to the anatomical features of the patient's skull (e.g. the Camper's plane) cannot be made directly. Direct transmission of face bow information is not supported.

Other CAD/CAM solutions support the direct transfer of plaster models which are cast into a physical articulator, further into a virtual articulator. For this purpose, the virtual counterpart matching to the respective physical articulator is stored in the software. The plaster models are removed from the physical articulator and inserted into a transfer holder (Amann Girrbach) or mounted on a transfer plate (3Shape) and inserted into the associated surface scanner. The geometric relation between the transfer holder and the articulator is stored in the software. Scanning captures the relative position of the plaster model to the transfer holder. With this information, the scanned jaw models can be positioned and aliened in the correct state in the virtual articulator. The disadvantage of this solution is that plaster models must first be created and physically articulated with the method described above.

DE102009044147A1 (Broghammer and Noack, Amann Girrbach AG) discloses to transfer the bite fork with the impression of the upper jaw into a transfer holder, similarly to that for a physical articulator. The bite fork is then scanned in this transfer holder. With the geometric parameters of the transfer holder in relation to the virtual articulator, which are stored in the software, the impression scan can be transferred directly into the virtual articulator. For this method, a transfer holder matching to the respective articulator model is still required.

WO2016034672 (Fisker et al., 3Shape AS) discloses a face bow with a movable pin which can be related to the tooth structure of the patient's upper jaw. On the face bow, a position marker is also attached. First, the face bow is attached to the patient's head and the pin aligned and fixed accordingly. With a 3D scanner a 3D model of the pin is created in relation to the patient's dentition. This model mast also include the position marker attached to the face how. The recorded 3D model is made to coincide with a 3D model of the face bow stored in the system. Thus, the geometric transformation between the patient's dentition and the face bow is known. This can be used for the transfer of the dental prosthesis model in the virtual articulator. Advantage of this method is that the face bow information can be transferred directly into the virtual articulator without the creation of physical impressions and without the creation of plaster models. However, capturing of the 3D model of the face bow relative to the patient's dentition with a 3D scanner e.g., an intraoral surface scanner can be quite expensive.

In other systems e.g. face hunter with plane System®, Zirkon Zahn, the patient head is detected with a 3D surface scanner (face scanner), and the anatomical features e.g.

Camper's plane are derived from the 3D model directly or determined by an additionally recorded face bow. To establish the relationship between the 3D model of the patient's head and the 3D model of the dentition a bite fork with a position marker protruding from the patient's mouth, is inserted into the patient's mouth. The position marker is detected in the 3D model of the patient's head. A surface scan of the bite fork determines the relation between the dentition model and the position marker and over this the relation between dentition model and head model of the patient.

Furthermore, the so-called jaw motion tracking systems make it possible to detect not only the static articulation data but also the dynamic articulation data, for example, SiCAT or Zebris. Here, a face bow is attached to the skull and aligned. In addition, a counterpart is fixed to the lower jaw of the patient. The lower jaw contains position markers, which are detected by sensors on the face bow. Hereby the movement of the lower jaw can be determined relative to the patient's skull and thus to the upper jaw. From these patient-specific trajectories, all articulation-relevant data can be derived.

SUMMARY OF THE INVENTION

An objective of the present invention is to overcome the disadvantages of the prior art and to make it possible to measure the patient-specific temporomandibular joint relation in a less complex way, and to transfer it into a virtual articulator or a physical articulator.

This objective has been achieved by any of the methods defined in claims 1 and 2. The subject-matter of the dependent claims define further achievement of the present invention.

According to the present invention, at least one form-fitting component (herein after called the first form-fitting component) which is fixed at the lower end of a transfer linkage is used for releasably leaving an impression on the impression material to be poured onto the grip of an impressions means such as a bite fork projecting out of the mouth of a patient. Thereby the position and orientation of the face bow can be directly transmitted e.g., by a dentist into the impression of the upper jaw on the impression means or into an impression next to the impression of the upper jaw on the impression means. After the impression material has cured, the first form-fitting component is released from its impression on the impression means by pulling it apart. After sending the impression means to a dental laboratory, the impression of the first form-fitting component and at least part of the impression of the upper jaw on the impression means is detected via a surface scanner, digitally recorded and thus the jaw models can be positioned in a patient-specific way into the virtual articulator. Herein, the information on the position and the alignment of the face bow is transferred to the impression means via the impression generated by the first form-fitting component. The first form-fitting component must be shaped so that the information is imprinted as precisely as possible into the impression material. For detecting the position, alternatively a scanbody with the shape of the first form-fitting component may be introduced into the impression. For a correct determination of the transformation between the upper jaw model and the virtual articulator, the transformation between the form-fitting component, the face bow and the virtual articulator must be beforehand deposited in the computer system governing the virtual articulator. If the transfer linkage is constructed considering the face bow and the virtual articulator, then this transformation can be derived directly from the CAD data and subsequently deposited in the computer system. Hence, the present invention makes it possible to capture the patient-specific temporomandibular joint relation in a less complex manner over known methods and to transfer it into the virtual articulator. Digital dental prostheses based on the patient-specific temporomandibular joint relationship can be better simulated, require less post-processing and are accepted more quickly by the patient. This also applies to other dental appliances such as bite splints. The technique of the present invention is not limited to virtual articulators and can also be applied to physical articulators. For example, after sending the impression means to the laboratory, the impression means can be joined with a copy of the transfer linkage in the physical articulator, and subsequently the upper/lower jaw model can be positioned in the coned position in the physical articulator. Thus, the dentist must send the impression means to the dental laboratory, but the transfer linkage may remain with the dentist for further use.

According to the present invention it is also possible to use an additional form-fitting component (hereinafter called the second form-fitting component) which can be releasably and form-fittingly engaged with the first form-fitting component and fixed into the impression material to be poured on the grip of the impression means projecting out of the mouth of the patient. Thereby the position and orientation of the face bow can be directly transmitted e.g. by the dentist into the impression means. The second form-fitting component is thereby connected to the impression means by the impression material and remains there and can be detected with a surface scanner together with the impression of the upper jaw. Hereby, the geometric relationship between the upper jaw model and the cranial reference plane determined by the face bow is known and can be used to set up the virtual articulator. The second form-fitting component is designed so that there is a clear geometric relationship between itself and its matching counterpart on the transfer linkage. In addition, it is designed so that its position and orientation can be clearly determined with a surface scanner. After sending the impression means to the laboratory, the surface of the second form-fitting component and at least part of the impression of the upper jaw can be detected via the surface scanner and the jaw models can be positioned in a patient-specific way into the virtual articulator.

According to the present invention the transfer of the face bow information into the virtual articulator takes place in two major steps. In the first step, the face bow information is transferred to the impressions means through the impression generated by the $1^{st}$ form-fitting component thereon or through the $2^{nd}$ form-fitting component plastered thereon. In the second major step, a model of the impression means is created by a surface scanner, the jaw models are digitized and transferred to the virtual articulator by using the model of the impression and the deposited transformation. The first major step may be performed at the dentist whereas the second major step may be performed in the dental laboratory. However, the method is also suitable for the pure chairside supply when using an intraoral scanner.

The present invention provides the ability to directly transfer the face bow information, to CAD/CAM wherein the position and alignment of the models can be directly derived from the scan of the impression means. This eliminates the need to first set up the plaster models in a physical articulator and then to transfer their orientation into the virtual articulator. When using the impression means scans, it is also possible to completely dispense with the production of the plaster models. According to the present invention, through transferring the face bow information to the impression means, the position and the orientation can be determined with an existing surface scanner. There are no additional measuring devices necessary. The dentist must only send the impression means to the dental laboratory. The face bow and the transfer linkage can remain with the dentist and can be further used. The present invention can also be realized with arbitrary face bows and physical/virtual articulators. By means of calibration also unknown facial bows can be integrated into the system. The present invention can be used with any face bow or a similar device which is able to determine the cranial reference plane and can be linked with the transfer linkage. Thus, established methods for measuring the temporomandibular joint relation can be further optimized and digitized between the dental practice and the laboratory.

According to the present invention the impression means may be a bite fork, an impression tray or a dual-arch impression tray.

According to the present invention the first and the second form-fitting components may have one or more recesses and/or one or more projections. These recesses and projections may have round or cornered shapes.

According to the present invention the transfer linkage having the first form-fitting component at its lower end is designed so that when the face bow is fixed to the head of the patient, the lower end of the transfer linkage is located near the grip of the impressions means projecting out of the mouth of the patient. The transfer linkage may be rigid. Alternatively, to facilitate locating the transfer linkage relative to the grip of the impression means, the transfer linkage may be adjustable through one or more adjustment means to allow changing the position of its lower end in the height direction and/or horizontal direction. The adjustment means may include a joint mechanism a screw mechanism and/or a sliding mechanism for the adjustment. The adjusted position may be read though a reading means such as scale or the like. The values of each scale must be read and transferred to the physical/virtual articulator.

According to the present invention to represent different distances between the face bow and the impression means, several rigid or adjustable transfer linkages of different lengths may be provided if required. The transfer linkage may include one or more rods or at least partly straight and partly curved bars which extend from the face bow towards the grip of the impressions means. The grip of the impression means is designed so large that the transfer of the face bow position and alignment is possible for all anatomical situations. The rods/bars may be aligned vertically and/or horizontally to point towards the head of the patient, particularly towards the grip of the impression means. The rods/bars may be rigidly or adjustably attached to the face bow. The rods/bars may be rigidly or adjustably attached to each other. The first form-fitting component may be rigidly or adjustably attached to the end of the vertical or horizontal rod/bar. The set of lengths of the transfer linkage, particularly the set of lengths of the rods/bars mast be transferred to the virtual articulator in each case, the adjusted positions must be read and transferred to the physical/virtual articulator.

BRIEF DESCRIPTION OF THE DRAWINGS

In the subsequent description, the present invention will be described in more detail by using exemplary embodiments and referring to the drawings, wherein FIG. 1—is a schematic view of a face bow, a transfer linkage and a bite fork according to the prior art.

DETAILED DESCRIPTION OF THE INVENTION

The reference numbers shown in the drawings denote the following elements which will be referred to in the subsequent description of the exemplary embodiments.

Figure 6:
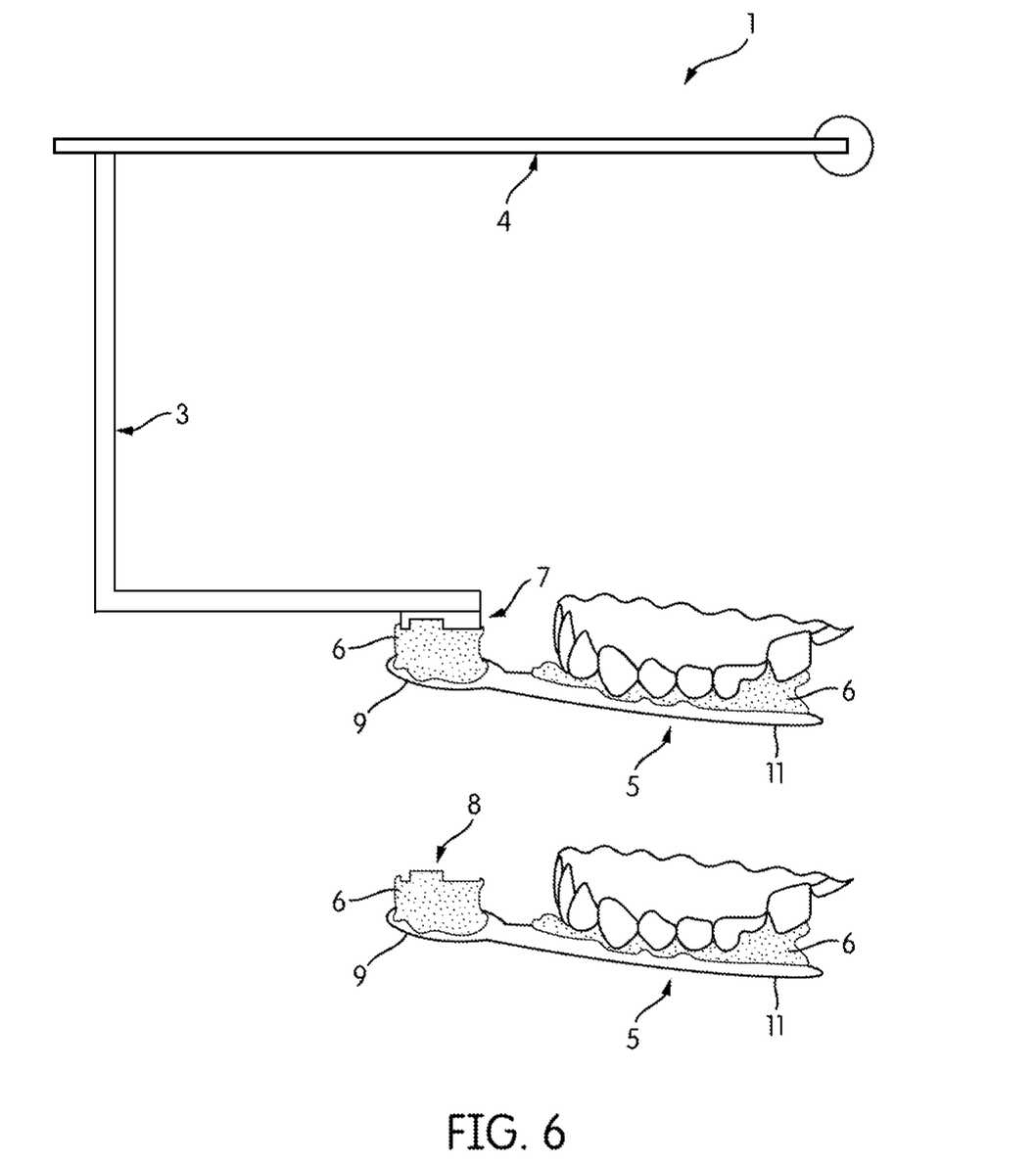
FIG. 6—is a schematic view of a device used in the process of leaving the impression of a first form-fitting component into the impression material on a bite fork according to a first embodiment of the present invention.

1. Device
2. Virtual articulator
3. Transfer linkage
4. Face bow
5. Impression means
6. Impression material
7. $1^{st}$ form-fitting component
8. Impression
9. Grip
10. $2^{nd}$ form-fitting component
11. Bite fork
12. Recess
12' Recess
13. Projection
13' Projection
14. Adjustment means
15. Reading means
16. $1^{st}$ rod
17. $2^{nd}$ rod
18. Slider
19. $1^{st}$ Slot
20. $2^{nd}$ Slot
21. Scale
Y: Height direction
X: Horizontal direction
C: Cranial reference plane FIG. 6 is a schematic view of the device (1) according to a first embodiment of the present invention for measuring patient-specific temporomandibular joint relation and transferring the same into a virtual articulator (2) or a physical articulator.

The device (1) has a transfer linkage (3), a face bow (4), and an impression means (5). The transfer linkage (3) is attached from its upper end to the face bow (4). The impression means (5) is suitable for holding impression material (6) and for taking the impression of the upper jaw and/or the lower jaw of the patient through said impression material (6). The device (1) has at least a first form-fitting component (7) fixed at the lower end of the transfer linkage (3), for releasably leaving an impression (8) on the impression material (6) to be placed on the grip (9) of the impressions means (5) projecting out of the mouth of the patient. The dentist uses the device (1) of FIG. 6 as follows. The impression means (5) such as a bite fork (11), an impression tray or a dual-arch impression tray is inserted into the mouth of the patient and fixed on the upper and/or lower jaw of the patient. Next, the face bow (4) is fixed on the patient's head and aligned according to the cranial reference plane (C). Thereafter, the transfer linkage (3) including at least a first form-fitting component (7) fixed at its lower end is attached to the face bow (4). Later silicone impression material (6) or the like is placed onto the grip (9) of the impression means (5) such that the first form-fitting component (7) leaves an impression (8). Depending on the type of the impression means (s) also the imprints of the upper and/or lower jaws are taken. For example, when using a bite fork (11) only the impression of the upper jaw is taken. After the imprint material (6) is cured the face bow (4), the transfer linkage (3) and the impression means (5) are removed from the patient. Finally, the first form-fitting component (7) is separated from the impression (8) in the impression means (5) as shown in the lower part of FIG. 6, and the impression means (5) is sent to the dental laboratory.

Figure 7:
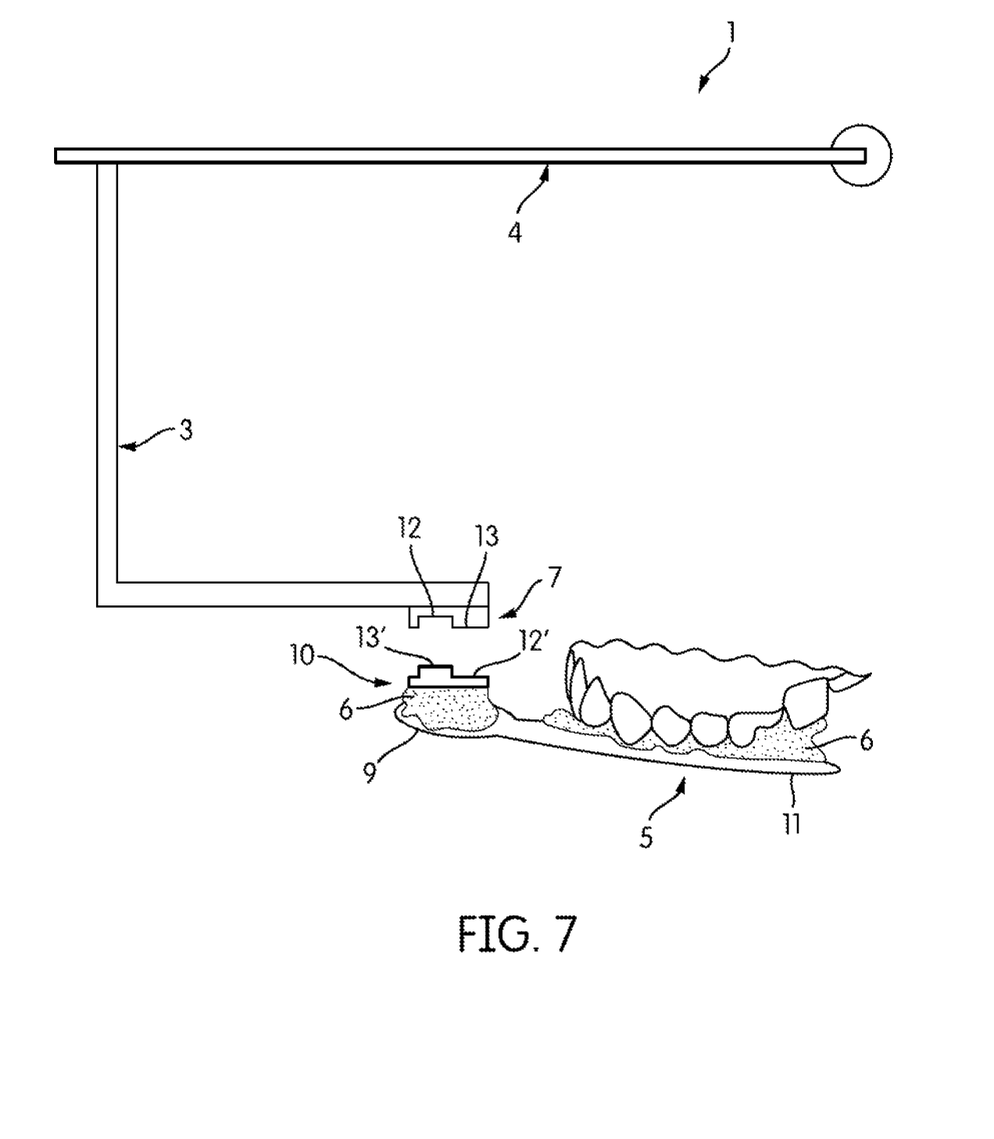
FIG. 7—is a schematic view of a device used in the process of plastering a second form fitting component on the bite fork through the impression material according to a second embodiment of the present invention.
Figure 8:
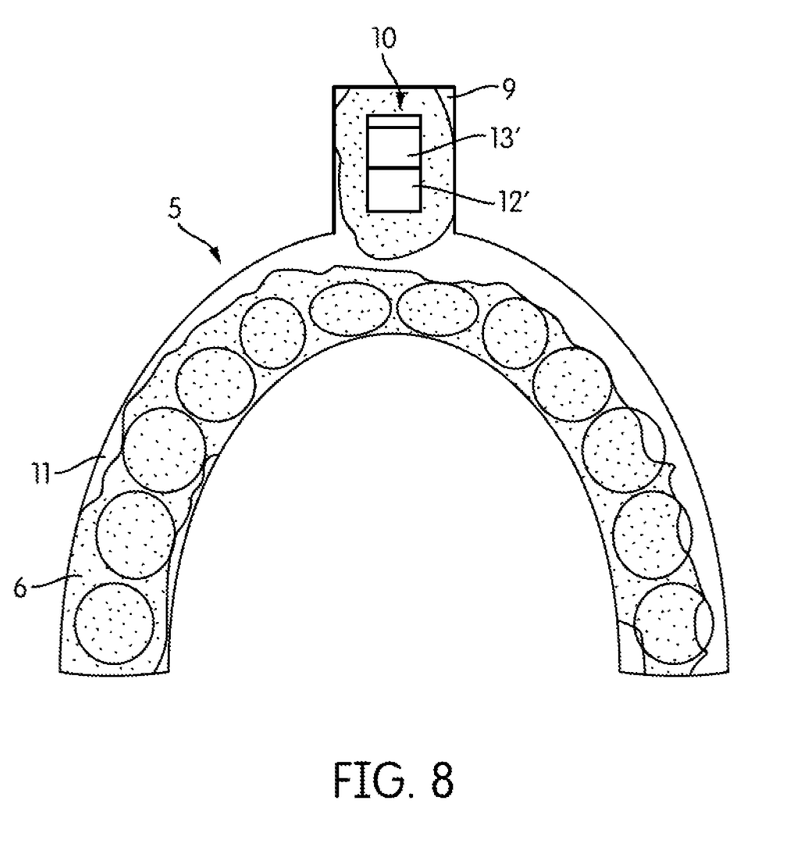
FIG. 8—is a schematic top view of the impression means of FIG. 7 having the second form fitting component plastered on the grip and the impression of the upper jaw.

FIG. 7 is a schematic view of the device (1) according to a second embodiment of the present invention for measuring patient-specific temporomandibular joint relation and transferring it into a virtual articulator (2) or a physical articulator. As shown in FIG. 7, the device (1) further includes a second form-fitting component (10) which can be releasably and form-fittingly engaged with the first form-fitting component (7). The second form-fitting component (10) can be plastered into the impression material (6) to be poured on the grip (9) of the impression means (5) projecting out of the mouth of the patient. The dentist uses the device (1) of FIG. 7 as follows. The impression means (5) such as a bite fork (11), an impression tray or a dual-arc impression tray is inserted into the mouth of the patient and fixed on the upper and/or lower jaw of the patient. Next, the face bow (4) is fixed on the patient's head and aligned according to the Camper's plane (C). Thereafter, the transfer linkage (3) including at least a first form-fitting component (7) fixed at the lower end, is attached to the face bow (4). Later the second form-fitting component (10) is releasably engaged with the first form-fitting component (7). Next, the second form-fitting component (10) is plastered to the impression means (5) with the help of silicone impression material (6) or the like when the first form-fitting component (7) and the $2^{nd}$ form-fitting component (10) are in the engaged state. Depending on the type of the impression means (5) also the impressions of the upper and/or lower jaw are taken. For example, when using a bite fork (11) only the impression of the upper jaw is taken. After curing, the face bow (4), the transfer linkage (3) and the impression means (5) are removed from the patient. Next, the second form-fitting component (10) together with the impression means (5) is separated from the first form-fitting component (7) fixed to the transfer linkage (3) as shown in the lower part of FIG. 7, and the impression means (5) is sent to the dental laboratory. FIG. 8 is a schematic top view of the impression means (5) of FIG. 7. As shown in FIG. 8 the impression means (5) holds the impression of the upper jaw and the second form fitting component fixed with the help of silicone impression material (6) or the like.

As shown in FIG. 7, the first form-fitting component (7) has a recess (12) and a projection (13) which engage with the projection (13') and the recess (12') of the second form-fitting component (10).

According to the present invention the transfer of the face bow (4) information, i.e., the position and the orientation, into the virtual articulator (2) or physical articulator takes place in two major steps. In the first major step, the position and orientation of the face bow (4) is transferred to the impressions means (5) through the impression (8) generated by the $1^{st}$ form-fitting component (7) thereon or through the $2^{nd}$ film-fitting component (10) plastered thereon. The first major step may be performed at the dentist. In the second major step, the information is transferred into the virtual articulator (2) or the physical articulator. The second major step may be performed in the dental laboratory.

To transfer the patient-specific temporomandibular joint relation into a virtual articulator (2), the dentist or dental technician uses the device (1) of FIG. 6 or 7 for the second major step as follows. Digital 3D models of the upper jaw and the lower jaw of the patient are created. Next the surface of the impression means (5) including at least part of the upper jaw impression and the surface of the impression (8) left by the first form-fitting component (7) (see FIG. 6) or the surface of the second form-fitting component (10) fixed with the help of impression material (6) to the impression means (5) (See FIG. 7) is detected by using a surface scanner, and thus a model of the impression means (5) is created. Next, the upper jaw model is correlated with the model of the impression means (5). This step can be omitted when an (individual) impression tray has been used as the impression means (5). Next, the transformation between the upper jaw model and the face bow (4) is determined based on the model of the impression means (5) and the deposited transformation between the first second form-fitting components (7,10) and the face bow (4). Next, the upper jaw model is transferred into the virtual articulator (2) by using the determined transformation. Next, the relation of the upper jaw model to the lower jaw model is determined. This step can be omitted when an (individual) dual-arch impression tray has been used. Next, the lower jaw model is transferred into the virtual articulator (2) according to the determined relation between upper jaw model and lower jaw model.

According to the present invention, digital 3D models of the upper jaw and lower jaw are created by directly recording in the patient's mouth with an intraoral scanner. Alternatively, digital 3D models of the upper jaw and lower jaw are created by recording previously generated silicone impressions or plaster models with an extraoral scanner. According to the present invention, the relation of the upper jaw model to the lower jaw are determined by recording the two jaws in the final bite position.

According to the present invention, the transfer of the face bow (4) information i.e., position and orientation can also be transferred into a physical articulator. To transfer the patient-specific temporomandibular joint relation into a physical articulator, the dentist or dental technician uses the device (1) of FIG. 6 or 7 for the second major step as follows. After the impression means (5) is sent to the dental laboratory, a copy/duplicate of the transfer linkage (3) is attached to the physical articulator. Next, the impression means (5) is joined with the copy of the transfer linkage (3) in the physical articulator. Next, the upper/lower jaw model are joined in the correct position in the physical articulator. Alternatively, the original transfer linkage (3) may be used.

As shown in FIG. 6 and FIG. 7 the transfer linkage (3) is rigid according to the first and second embodiments of the present invention.

Figure 9:
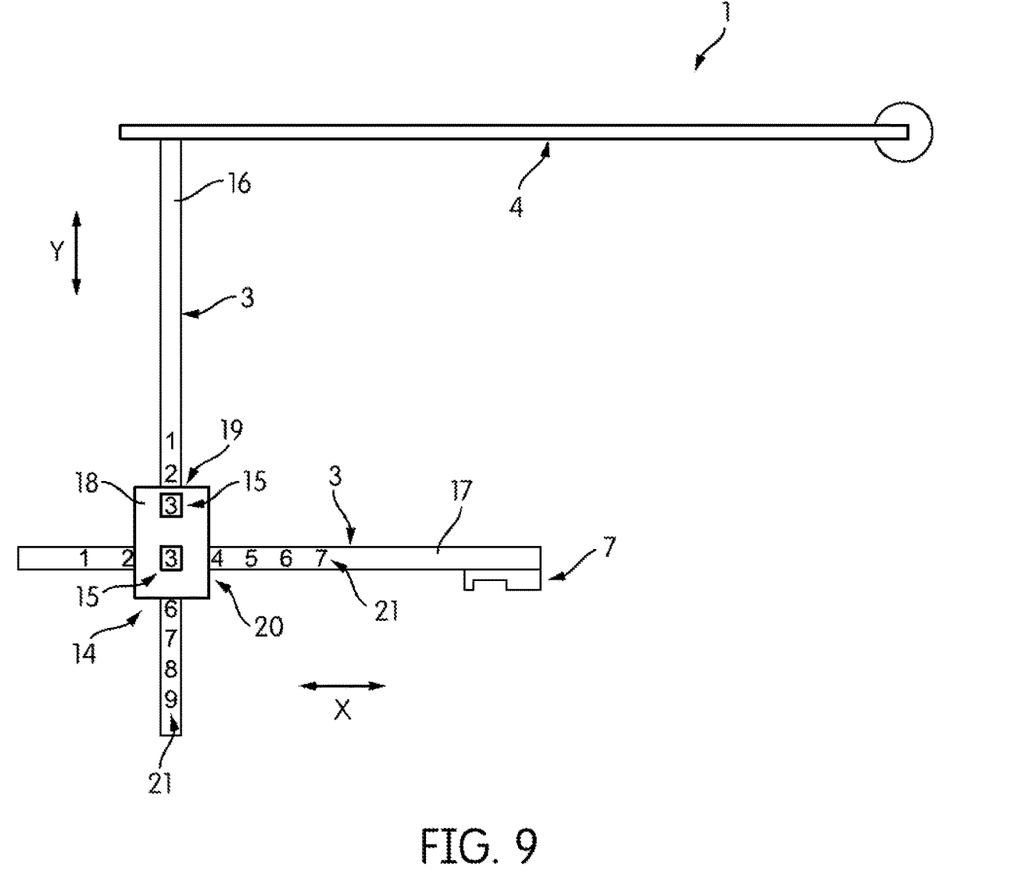
FIG. 9—is a schematic view of a device including a transfer linkage with an adjustment means according to a third embodiment of the present invention.

Alternatively, the device (1) in FIG. 6 and FIG. 7 may be provided with a transfer linkage (3) that is adjustable. FIG. 9 is a schematic view of the device (I) according to a third embodiment of the present invention which has adjustment means (14) adapted to selectively adjust the position of the lower end of the transfer linkage (3) in the height direction (Y) and the horizontal direction (X), and a reading means (15) adapted to read the position of the lower end of the transfer linkage (3) in the height direction (Y) and the horizontal direction (X). As shown in FIG. 9, the transfer linkage (3) comprises a first rod (16) which extends in the height direction (Y) and a second rod (17) which extends in the horizontal direction (X). As shown in FIG. 9, the first form-fitting component (7) is fixed at the end of the second rod (17). As shown in FIG. 9, the adjustment means (14) comprises a slider (18) which has a first slot (19) slidably engaged with the first rod (15), and a second slot (20) slidably engaged with the second rod (17). The reading means (18) has two scales (21) for reading the adjusted position of the first form-fitting component (7).

The invention claimed is:

1. A method of measuring patient-specific temporomandibular joint relation and transferring it into a virtual articulator, the method comprising:
   inserting an impression means such as a bite fork, an impression tray or a dual-arch impression tray into the mouth of a patient and fixing on the upper jaw;
   fixing a face bow on a patient's head and aligning according to a predefined cranial reference plane (C);
   fixing of a transfer linkage including at least a first form-fitting component fixed at a lower end of the transfer linkage, to the face bow;
   leaving an impression of the first form-fitting component with the help of silicone impression material or the like on a grip of the impression means;
   removing the face bow, the transfer linkage and the impression means from the patient;
   separating the first form-fitting component from the impression in the impression means;
   creating digital 3D models of the upper jaw and the lower jaw of the patient;
   detecting by using a surface scanner, the surface of the impression means including at least part of the upper jaw impression and the surface of the impression left by the first form-fitting component optionally with/without a scanbody inserted therein, thereby creating a model of the impression means;
   correlating the upper jaw model with the model of the impression means, wherein this step is dispensed with when using an impression tray;
   determining a transformation between the upper jaw model and the face bow based on the model of the impression means and a transformation between the first form-fitting component and the face bow;
   transferring of the upper jaw model into the virtual articulator using the determined transformation;
   determining the relation of the upper jaw model to the lower jaw model, wherein this step is dispensed with when using a dual-arch impression tray; and
   transferring the lower jaw model into the virtual articulator according to the determined relation between upper jaw model and lower jaw model.

2. The method according to claim 1, wherein the step of creating digital 3D models of the upper jaw and lower jaw of the patient includes:
   recording directly in the patient's mouth with an intraoral scanner, or
   generating with an extraoral scanner previously generated silicone impressions or plaster models, and wherein the step of determining the relation of the upper jaw model to the lower jaw model includes:
   recording of the two jaws in the final bite position.

3. The method according to claim 1, wherein the impression means comprises a bite fork, an impression tray or a dual-arch impression tray.

4. The method according to claim 1, wherein the first form-fitting component has one or more recesses and/or one or more projections.

5. The method according to claim 4, wherein the recess and the projection have matching rounded and/or cornered shapes.

6. The method according to claim 1, wherein the transfer linkage is rigid.

7. The method according to claim 1, wherein the device further comprises: an adjustment means for adjusting the position of the lower end of the transfer linkage in the height direction (Y); and a reading means for reading the position of the lower end of the transfer linkage in the height direction (Y).

8. The method according to claim 7, wherein the adjustment means is further adapted to selectively adjust the position of the lower end of the transfer linkage in the height direction (Y) and the horizontal direction (X), and the reading means is further adapted to read the position of the lower end of the transfer linkage in the height direction (Y) and the horizontal direction (X).

9. The method according to claim 8, wherein the transfer linkage comprises: a first rod which extends in the height direction (Y); and a second rod which extends in the horizontal direction (X), wherein at least the first form-fitting component is fixed at the end of the second rod, and wherein the adjustment means comprises a slider which has a first slot slidably engaged with the first rod, and a second slot slidably engaged with the second rod, and wherein the reading means comprises two scales for reading the position of the first form-fitting component.

10. A method of measuring patient-specific temporomandibular joint relation and transferring it into a virtual articulator, the method comprising:
   inserting an impression means such as a bite fork, an impression tray or a dual-arch impression tray into the mouth and fixing on the upper jaw;
   fixing a face bow on the patient's head and aligning according to a predefined cranial reference plane (C);
   fixing a transfer linkage including at least a first form-fitting component fixed at the lower end, to the face bow, fixing a component to the impression means with the help of silicone impression material or the like when the first form-fitting component and a second form-fitting component are in the engaged state, removing the face bow, the transfer linkage and the impression means from the patient;
   releasing the second form-fitting component from the first form-fitting component fixed to the transfer linkage;
   creating digital 3D models of the upper jaw and the lower jaw of the patient;
   detecting by using a surface scanner, the surface of the impression means including at least part of the upper jaw impression and the surface of the second form-fitting component fixed with the help of impression material to the impression means, thereby creating a model of the impression means;

correlating the upper jaw model with the model of the impression means, wherein this step is dispensed with when using an impression tray;

determining a transformation between the upper jaw model and the face bow based on the model of the impression means and a transformation between the first and second form-fitting components and the face bow;

transferring of the upper jaw model into the virtual articulator using the determined transformation;

determining the relation of the upper jaw model to the lower jaw model, wherein this step is dispensed with when using a dual-arch impression tray; and transferring the lower jaw model into the virtual articulator according to the determined relation between the upper jaw model and the lower jaw model.

11. The method according to claim 10, wherein the step of creating digital 3D models of the upper jaw and lower jaw of the patient includes: recording directly in the patient's mouth with an intraoral scanner, or generating with an extraoral scanner previously generated silicone impressions or plaster models, and wherein the step of determining the relation of the upper jaw model to the lower jaw model includes: recording of the two jaws in the final bite position.

12. The method according to claim 10, wherein the impression means comprises a bite fork or an impression tray or a dual-arch impression tray.

13. The method according to claim 10, wherein the first form-fitting component has one or more recesses and/or one or more projections.

14. The method according to claim 10, wherein the second form-fitting component has one or more projections and/or one or more recesses releasably and form-fittingly engaging respectively with the one or more recesses and/or one or more projections of the first form-fitting component.

15. The method according to claim 14 wherein the recess and the projection have matching rounded and/or cornered shapes.

16. The method according to claim 10, wherein the transfer linkage is rigid.

17. The method according to claim 10, wherein the device further comprises: an adjustment means for adjusting the position of the lower end of the transfer linkage in the height direction (Y); and a reading means for reading the position of the lower end of the transfer linkage in the height direction (Y).

18. The method according to claim 17, wherein the adjustment means is further adapted to selectively adjust the position of the lower end of the transfer linkage in the height direction (Y) and the horizontal direction (X), and the reading means is further adapted to read the position of the lower end of the transfer linkage in the height direction (Y) and the horizontal direction (X).

19. The method according to claim 18, wherein the transfer linkage comprises: a first rod which extends in the height direction (Y); and a second rod which extends in the horizontal direction (X), wherein at least the first form-fitting component is fixed at the end of the second rod, and wherein the adjustment means comprises a slider which has a first slot slidably engaged with the first rod, and a second slot slidably engaged with the second rod, and wherein the reading means comprises two scales for reading the position of the first form-fitting component.

* * * * *

UNITED STATES PATENT AND TRADEMARK OFFICE
CERTIFICATE OF CORRECTION

| | |
|---|---|
| PATENT NO. | : 12,150,823 B2 |
| APPLICATION NO. | : 17/430886 |
| DATED | : November 26, 2024 |
| INVENTOR(S) | : Rößler et al. |

Page 1 of 1

It is certified that error appears in the above-identified patent and that said Letters Patent is hereby corrected as shown below:

On the Title Page

Item (54) after "METHOD", insert --FOR MEASURING PATIENT-SPECIFIC--

In item (71), in "Applicant", in Column 1, Line 1, delete "inc.," and insert --INC.,-- therefor In the Specification In Column 1, Line 1, after "METHOD", insert --FOR MEASURING PATIENT-SPECIFIC--

Signed and Sealed this
Eleventh Day of February, 2025

Coke Morgan Stewart
*Acting Director of the United States Patent and Trademark Office*